(12) United States Patent
Vandenabeele et al.

(10) Patent No.: US 6,306,571 B1
(45) Date of Patent: *Oct. 23, 2001

(54) PHOTOTHERMOGRAPHIC RECORDING MATERIAL COATABLE FROM AN AQUEOUS MEDIUM

(75) Inventors: Hubert Vandenabeele, Mortsel; Herman Uytterhoeven, Bonheiden, both of (BE)

(73) Assignee: Agfa-Gevaert (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/999,409

(22) Filed: Dec. 29, 1997

Related U.S. Application Data

(60) Provisional application No. 60/038,762, filed on Feb. 20, 1997.

(30) Foreign Application Priority Data

Dec. 30, 1996 (EP) .................................................. 96203729

(51) Int. Cl.$^7$ .................................................. G03C 1/498
(52) U.S. Cl. ........................................... 430/617; 430/620
(58) Field of Search .................................... 430/617, 620, 430/619, 623; 554/74

(56) References Cited

U.S. PATENT DOCUMENTS

| | | |
|---|---|---|
| 3,457,075 | 7/1969 | Morgan et al. . |
| 3,839,049 | 10/1974 | Simons . |
| 3,856,527 | 12/1974 | Hamb et al. . |
| 3,897,935 | 8/1975 | Forster et al. . |
| 3,960,908 * | 6/1976 | Ikenoue et al. ........................ 430/620 |
| 4,152,162 | 5/1979 | Masuda et al. . |
| 4,188,212 * | 2/1980 | Fujiwara et al. ........................ 403/69 |
| 4,210,717 | 7/1980 | Gatzke . |
| 4,273,723 | 6/1981 | Hayashi et al. . |
| 4,307,187 * | 12/1981 | Ikenoue et al. ........................ 430/619 |
| 4,473,504 | 9/1984 | Odashima . |
| 4,476,220 | 10/1984 | Penfound . |
| 5,364,733 * | 11/1994 | Kenny et al. ........................ 430/203 |
| 5,747,412 * | 5/1998 | Leenders et al. ........................ 503/201 |
| 5,891,616 | 4/1999 | Gilliam et al. . |
| 6,159,667 | 12/2000 | Emmers et al. . |

FOREIGN PATENT DOCUMENTS

| | | |
|---|---|---|
| 877108 | 10/1979 | (BE) . |
| 0754969 | 7/1996 | (EP) . |
| 0848286 | 12/1997 | (EP) . |
| 1347350 | 7/1971 | (GB) . |
| 2002917A | 2/1979 | (GB) . |

OTHER PUBLICATIONS

Chemical Data, Aylward & Findlay.
Database abstract of J58028737.

* cited by examiner

*Primary Examiner*—Thorl Chea
(74) *Attorney, Agent, or Firm*—Leydig, Voit & Mayer, Ltd.

(57) ABSTRACT

A process for producing an aqueous dispersion I containing particles including a substantially light-insensitive organic heavy metal salt A with a solubility in 100 mL of water of less than $10^{-3}$ g at 20° C. comprising the steps of: (i) producing an aqueous dispersion II containing particles containing a salt B with a solubility in 100 mL of water between 1.5 g and 0.001 g at 20° C.; and (ii) converting the salt B in the particles of the aqueous dispersion II into the organic heavy metal salt A, wherein the organic heavy metal salt A and the salt B have a common cation; and a production process for thermographic and photothermographic materials therewith.

12 Claims, No Drawings

PHOTOTHERMOGRAPHIC RECORDING MATERIAL COATABLE FROM AN AQUEOUS MEDIUM

The application claims the benefit of U.S. Provisional Application No.60/038,762 filed Feb. 20, 1997.

DESCRIPTION

1. Field of the Invention

The present invention relates to a photothermographic recording material comprising a photo-addressable thermosensitive element coatable from aqueous media.

2. Background of the Invention

Thermal imaging or thermography is a recording process wherein images are generated by the use of thermal energy. In direct thermal thermography a visible image pattern is formed by imagewise heating of a recording material containing matter that by chemical or physical process changes colour or optical density. Such materials become photothermographic by incorporating a photosensitive agent which after exposure to UV, visible or IR light is capable of catalyzing or participating in a thermographic process bringing about changes in colour or optical density.

Examples of photothermographic materials are the so called "Dry Silver" photographic materials of the 3M Company, which are reviewed by D. A. Morgan in "Handbook of Imaging Science", edited by A. R. Diamond, page 43, published by Marcel Dekker in 1991.

U.S. Pat. No. 4,473,504 discloses a method of producing granular metallic soap characterized in that a water-insoluble metal carbonate and a fatty acid, in a water-dispersed state, are reacted by heating the dispersion at a temperature above the temperature above the temperature at which the fatty acid begins to melt but below the melting point of the metallic soap to be formed until the metal carbonate in the reaction system has disappeared and the generation of bubbles of by-produced carbon dioxide gas is no longer observed, stopping the heating, recovering the resultant metallic soap in the form of porous granules by filtration, washing the metallic soap and then drying the same.

The standard teaching over thermographic materials based on a substantially light-insensitive organic heavy metal salt and a reducing agent for the organic heavy metal salt and photothermographic materials which additionally have photosensitive silver halide in intimate catalytic association with the organic heavy metal salt is that the organic heavy metal salt is formed in a mixture of water and an organic solvent and is precipitated and dried before dispersion in an organic solvent medium from which the dispersion is coated. In the case of photothermographic materials, the silver halide is either prepared ex situ and is added to a dispersion of the organic heavy metal salt as described in U.S. Pat. No. 3,080,254 or is present during the formation of the organic heavy metal salt as disclosed in U.S. Pat. No. 3,839,049, or is prepared in situ from an organic silver salt by reaction with a halide ion source as disclosed in U.S. Pat. No. 3,457,075.

This production method is very inefficient as the organic heavy metal salt formed has to be separated and dried before dispersion in a solvent medium, is environmentally unsound as evaporation of solvent takes place during the coating process and it involves lengthy utilization of plant during the preparation of the organic heavy metal salt dispersion and coating requires costly plant due to the need for solvent explosion prevention measures and solvent recovery to prevent solvent emission to the environment. Furthermore, in the case of photothermographic materials, it is desirable spectrally to sensitize photosensitive silver halide in water-containing media as this permits the use of a broader range of spectrally sensitizing dyes.

Research Disclosure number 17029, published in June 1978, in section II gives a survey of different methods of preparing organic heavy metal salts. Method 5, for example, describes the preparation of silver behenate by (a) heating behenic acid in water to a temperature above the melting point of the acid, but below the boiling point of the dispersion, (b) adding an aqueous solution of alkali metal or ammonium hydroxide, and (c) adding an aqueous solution of silver nitrate. However, in order to obtain a fine emulsion of an organic heavy metal salt, either the synthesis has to be carried out in an organic solvent medium as disclosed, for example, in U.S. Pat. No. 3,700,458 or in a mixture of water and a substantially water insoluble organic solvent as disclosed, for example, in U.S. Pat. No. 3,960,908 for silver carboxylates or in GB-P 1,173,426 for the silver salt of benzotriazole.

For ecological and economic reasons, a process is therefore required for producing particles comprising a substantially light-insensitive organic heavy metal salt as aqueous dispersions of fine non-agglomerated particles, which can be used directly in producing aqueous coating dispersions for thermographic and photothermographic materials.

OBJECTS OF THE INVENTION

It is a first object of the invention to provide a production process for aqueous dispersions of particles comprising a substantially light-insensitive organic heavy metal salt.

It is a second object of the invention to provide a production process for aqueous dispersions of particles comprising a substantially light-insensitive organic heavy metal salt which can be used directly in producing coating dispersions for thermographic and photothermographic materials.

It is another object of the present invention to provide a production process for thermographic and photothermographic materials utilizing such aqueous dispersions comprising particles comprising a substantially light-insensitive organic heavy metal salt.

Further objects and advantages of the invention will become apparent from the description hereinafter.

SUMMARY OF THE INVENTION

A process is provided, according to the present invention, for producing an aqueous dispersion I containing particles including a substantially light-insensitive organic heavy metal salt A with a solubility in 100 mL of water of less than $10^{-3}$ g at 20° C. comprising the steps of: (i) producing an aqueous dispersion II containing particles including a salt B with a solubility in 100 mL of water between 1.5 g and 0.001 g at 20° C.; and (ii) converting the salt B in the particles of the aqueous dispersion II into the substantially light-insensitive organic heavy metal salt A, wherein the organic heavy metal salt A and the salt B have a common cation.

A process is also provided, according to the present invention, for producing a thermographic material comprising the steps of: (i) coating a support with one or more aqueous dispersions or solutions which together comprise an aqueous dispersion I containing particles including a substantially light-insensitive organic heavy metal salt A with a solubility in 100 mL of water of less than $10^{-3}$ g at 20° C. produced as described above, an organic reducing agent and a binder including a water-dispersible binder, a water-soluble binder or a mixture of a water-dispersible binder and a water-soluble binder; ii) drying the resulting one or more coatings to produce a thermosensitive element.

A process for producing a thermographic material as described above, wherein the thermosensitive element, as described above, further comprises photosensitive silver halide in catalytic association with the organic heavy metal salt A.

Preferred embodiments of the present invention are disclosed in the detailed description of the invention.

DETAILED DESCRIPTION OF THE INVENTION

Aqueous

The term aqueous for the purposes of the present invention includes mixtures of water with water-miscible organic solvents such as alcohols e.g. methanol, ethanol, 2-propanol, butanol, iso-amyl alcohol, octanol, cetyl alcohol etc; glycols e.g. ethylene glycol; glycerine; N-methyl pyrrolidone; methoxypropanol; and ketones e.g. 2-propanone and 2-butanone etc.

Production of an aqueous dispersion of particles comprising a substantially water-insoluble organic heavy metal salt A process is provided, according to the present invention, for producing an aqueous dispersion I containing particles including an organic heavy metal salt A with a solubility in 100 mL of water of less than $10^{-3}$ g at 20° C. comprising the steps of: (i) producing an aqueous dispersion II containing particles including a salt B with a solubility in 100 mL of water between 1.5 g and 0.001 g at 20° C.; and (ii) converting the salt B in the particles of the aqueous dispersion II into the organic heavy metal salt A, characterized in that the organic heavy metal salt A and the salt B have a common cation.

In preferred embodiments of the present invention, the solubility of organic heavy metal salt A in 100 mL of water is less than $5\times10^{-4}$ g at 20° C. and the solubility of salt B in 100 mL of water is between 0.5 g and 0.005 g at 20° C.

The aqueous dispersion II may be produced by any techniques known from the prior art, for example addition of an aqueous solution to another aqueous solution or simultaneous addition of two aqueous solution to a recipient. The addition of these solutions may or may not be metered and in the case of simultaneous metered addition of the two solutions may be regulated by the concentration of cations or the concentration of anions of the salt in the suspending medium. The choice of configuration used, the concentration of the solutions, the rate of addition and the temperatures of the solutions and the suspending medium will all influence the particle size distribution of the particles comprising the salt B in aqueous dispersion II.

The aqueous dispersion I containing particles including an organic heavy metal salt A may be produced from an aqueous dispersion II containing particles including a salt B by any techniques known from the prior art, for example addition of an aqueous solution of a salt having the same cation as the organic heavy metal salt A to the aqueous dispersion II; or simultaneous addition of an aqueous solution of a salt having the same cation as the organic heavy metal salt A and the aqueous dispersion II to a recipient. The addition of these solutions and aqueous dispersion II may or may not be metered and in the case of simultaneous metered addition may be regulated by the concentration of the cations or the concentration of the anions of the heavy metal salt A or by the pH of the dispersion in the recipient. The choice of configuration used, the concentration of the solution and dispersion, the rate of addition and the temperatures of solution, dispersion and suspending medium will all influence the particle size distribution of the particles comprising the heavy metal salt A in aqueous dispersion I.

During or after completion of the production of aqueous dispersion I, water-soluble salts produced during the process and any excess dissolved ions, for example silver ions, may be removed by on-line or off-line desalting processes such as dialysis or ultrafiltration. Desalting of the suspension may also be achieved after completion of the production process by precipitation of the suspension, followed by decantation, washing and redispersion.

A process according to the present invention may be carried out batchwise or in continuous mode in any suitable recipient.

The particles comprising a substantially light-insensitive organic heavy metal salt A, of the present invention, may contain several molecular species, such as: substantially light-insensitive organic heavy metal salts; photosensitive agents; organic compounds e.g. organic carboxylic acids, dicarboxylic acids etc.; salts of organic compounds e.g. salts of organic carboxylic acids; stabilizers; antifoggants etc., the molecular species being randomly distributed in the particles or incorporated in a predetermined microstructure. The particles may also be used in mixtures with light-insensitive organic heavy metal salt-containing particles prepared using prior art technology.

Sparingly Soluble Salts

Salts B with a solubility in 100mL of water of between 1.5 g and 0.001 g at 20° C. are preferred according to the present invention with salts B with a solubility in 100 mL of water of between 0.5 g and 0.01 g at 20° C. being particularly preferred.

Suitable salts B present in the particles of dispersion II with the same cation as salt A, according to the present invention, are, for example, silver acetate, silver propionate, silver butyrate, silver isobutyrate, silver tartrate, silver salicylate, silver malonate, silver succinate and silver oxalate. The solubilities of some of these salts are given below:

|  | Solubility in water at 20° C. in g/100 mL water |
|---|---|
| silver acetate | 1.04 |
| silver propionate | 0.83 |
| silver sulfate | 0.57 (at 0° C.) |
| silver butyrate | 0.48 |
| silver metaphosphate | 0.32 |
| silver benzoate | 0.217 |
| silver tartrate | 0.201 (at 18° C.) |
| silver bromate | 0.20 |
| silver nitrite | 0.16 (at 0° C.) |
| silver selenate | 0.118 |
| silver salicylate | 0.08 (at 18° C.) |
| silver hyponitrite | 0.075 (at 13° C.) |
| silver malonate | 0.057 |
| silver tungstate | 0.05 (at 15° C.) |
| silver succinate | 0.0176 (at 18° C.) |
| silver oxalate | 0.00339 (at 18° C.) |
| silver iodate | 0.003 |

Conversion Agents

Suitable agents for converting salt B in the particles of the aqueous dispersion II into the organic heavy metal salt A are water-soluble salts with the anion of salt A and a cation which forms a water-soluble salt with the anion of salt B.

For the case of salt B being silver salicylate and salt A being silver behenate, for example, a suitable conversion agent would be sodium behenate. Were salt B to be silver salicylate and salt A to be silver benzotriazolate, then sodium benzotriazolate would be a suitable conversion agent.

Light-insensitive Organic Heavy Metal Salts

The term heavy metal, for the purposes of the present invention, includes the noble metals, such as silver and gold, and the transition metals, such as iron, cobalt, nickel, manganese etc., with silver being preferred.

Preferred substantially light-insensitive heavy metal salts A with a solubility in 100 mL of water of less than $10^{-3}$ g at 20° C. present in the particles produced using the process according to the present invention and used in the production of thermographic materials, according to the present invention, are silver salts of organic carboxylic acids having as their organic group: aryl, aralkyl, alkaryl or alkyl. For example aliphatic carboxylic acids known as fatty acids, wherein the aliphatic carbon chain has at least 12 C-atoms, e.g. silver laurate, silver palmitate, silver stearate, silver hydroxystearate, silver oleate and silver behenate, which silver salts are also called "silver soaps". The solubilities of some of these silver salts are given below:

|  | Solubility in water at 20° C. in g/100 mL water |
| --- | --- |
| silver stearate | $6.5 \times 10^{-5}$ |
| silver palmitate | $1.2 \times 10^{-4}$ |

Silver salts of modified aliphatic carboxylic acids with thioether group, as described e.g. in GB-P 1,111,492, may likewise be used to produce a thermally developable silver image.

Furthermore, heavy metal salts of organic compounds with an acidic —N—H group may be used according to the present invention. Preferred examples of these compounds include silver salts of benztriazole and derivatives thereof; silver salts of halogen-substituted benzotriazoles; silver salts of carboimidobenzo-triazoles; silver salts of 1,2,4-triazoles or 1-H-tetrazoles as described in U.S. Pat. No. 4,220,709; silver salts of imidazoles and imidazole derivatives; other organic silver salts as described in GB-P 1,439,478, e.g. silver phthalazinone; etc. Further are mentioned silver imidazolates and the substantially light-insensitive inorganic or organic silver salt complexes described in U.S. Pat. No. 4,260,677. Other suitable organic heavy metal salts, according to the present invention, are silver salts complexed with coordinating compounds having a gross stability constant between 4.50 and 10.00, as disclosed in U.S. Pat. No. 4,260,677.

Useful substantially light-insensitive organic iron salts are e.g. iron salts of an organic acid, e.g. the iron salts described in EP-A 520 404.

A useful substantially light-insensitive organic nickel salt, nickel stearate, is described in CA-P 763,903.

In a preferred embodiment, according to the present invention, the substantially light-insensitive organic heavy metal salt is a silver salt and in particular a silver salt of an organic carboxylic acid or silver benzotriazolate.

The term substantially light-insensitive organic heavy metal salt for the purposes of the present invention also includes mixtures of organic heavy metal salts.

Thermosensitive Element

A thermosensitive element, according to the present invention, comprises a substantially light-insensitive organic heavy metal salt with a solubility in 100 mL of water of less than $10^{-3}$ g at 20° C., an organic reducing agent therefor in thermal working relationship therewith and a binder comprising a water-soluble binder, a water-dispersible binder or a mixture of a water-dispersible and a water-soluble binder. The thermosensitive element may comprise a layer system with the substantially light-insensitive organic heavy metal salt and the other ingredients active in the thermal development process or pre- or post-development stabilization of the element being in the same layer or in other layers with the proviso that the organic reducing agent and the toning agent, if present, are in thermal working relationship with the substantially light-insensitive organic heavy metal salt i.e. during the thermal development process the reducing agent and the toning agent, if present, are able to diffuse to the substantially light-insensitive organic heavy metal salt.

The thermosensitive element becomes photo-addressable upon the addition of photosensitive silver halide in catalytic association with the substantially light-insensitive organic heavy metal salt and may further comprise spectral sensitizer optionally together with a supersensitizer in intimate sensitizing association with the photosensitive silver halide.

Organic Reducing Agent

Suitable organic reducing agents for the reduction of the substantially light-insensitive organic heavy metal salts are organic compounds containing at least one active hydrogen atom linked to O, N or C. Particularly suitable organic reducing agents for the reduction of the substantially light-insensitive organic heavy metal salts A are reductones, such as ascorbic acid, and non-sulfo-substituted 6-membered aromatic or heteroaromatic ring compounds with at least three substituents one of which is a hydroxy group at a first carbon atom and a second of which is a hydroxy or amino-group substituted on a second carbon atom one, three or five ring atoms removed in a system of conjugated double bonds from the first carbon atom in the compound, in which (i) the third substituent may be part of an annelated carbocyclic or heterocyclic ring system; (ii) the third substituent or a further substituent is not an aryl- or oxo-aryl-group whose aryl group is substituted with hydroxy-, thiol- or amino-groups; and (iii) the third substituent or a further substituent is a non-sulfo-electron withdrawing group if the second substiuent is an amino-group.

In preferred reducing agents, the ring atoms of the non-sulfo-substituted 6-membered aromatic or heteroaromatic ring compound consist of nitrogen and carbon ring atoms and the non-sulfo-substituted 6-membered aromatic or heteroaromatic ring compound is annulated with an aromatic or heteroaromatic ring system.

In further preferred reducing agents, the non-sulfo-substituted 6-membered aromatic or heteroaromatic ring compound is substituted with one or more of the following substituents which may also be substituted: alkyl, alkoxy, carboxy, carboxy ester, thioether, alkyl carboxy, alkyl carboxy ester, aryl, sulfonyl alkyl, sulfonyl aryl, formyl, oxo-alkyl and oxo-aryl.

Particularly preferred reducing agents are ascorbic acid and substituted catechols or substitued hydroquinones with 3-(3', 4'-dihydroxyphenyl)propionic acid, 3',4'-dihydroxybutyrophenone, methyl gallate, ethyl gallate and 1,5-dihydroxy-naphthalene being especially preferred.

During the thermal development process the reducing agent must be present in such a way that it is able to diffuse to the particles comprising a substantially light-insensitive organic heavy metal salt A so that reduction thereof can take place.

Auxiliary Reducing Agents

The above mentioned reducing agents, regarded as primary or main reducing agents, may be used in conjunction with so-called auxiliary reducing agents. Auxiliary reducing agents that may be used in conjunction with the above mentioned primary reducing agents are sulfonyl hydrazide reducing agents such as disclosed in U.S. Pat. No. 5,464, 738; trityl hydrazides and formyl-phenyl-hydrazides such as disclosed in U.S. Pat. No. 5,496,695 and the combination thereof with amine compounds as disclosed in U.S. Pat. No. 5,545,505, hydroxamic acid compounds as disclosed in U.S. Pat. No. 5,545,507, acrylonitrile compounds as disclosed in U.S. Pat. No. 5,545,515 and N-acyl compounds as disclosed in U.S. Pat. No. 5,558,983; and organic reducing metal salts, e.g. stannous stearate described in U.S. Pat. Nos. 3,460,946 and 3,547,648.

Water-dispersible and Water-soluble Binders

According to the present invention the thermosensitive element comprises a binder comprising a water-soluble binder, a water-dispersible binder or a mixture of a water soluble binder and a water-dispersible binder.

In a preferred embodiment of the present invention the binder is a polymer latex. The production of polymer latexes is described in the "Kirk-Othmer Encyclopedia of Chemical Technology, Fourth Edition", published by John Wiley & Sons, New York in 1995, pages 51 to 68; "Emulsion Polymerization", by D. C. Blackley, published by Applied Science, London in 1975; contribution by G. Lichti, R. G. Gilbert and D. H. Napper in "Emulsion Polymerization", edited by I. Piirma and published by Academic Press in 1982; and the contribution by D. H. Napper and R. G. Gilbert in "Comprehensive Polymer Science", edited by G. C. Eastmond, A. Ledwith, S. Russo and P. Sigwalt and published by Pergamon Press, New York in 1989.

The water-dispersible binder can be any water-insoluble polymer e.g. water-insoluble cellulose derivatives, polymers derived from α,β-ethylenically unsaturated compounds such as polyvinyl chloride, after-chlorinated polyvinyl chloride, copolymers of vinyl chloride and vinylidene chloride, copolymers of vinyl chloride and vinyl acetate, polyvinyl acetate and partially hydrolyzed polyvinyl acetate, polyvinyl alcohol, polyvinyl acetals that are made from polyvinyl alcohol as starting material in which only a part of the repeating vinyl alcohol units may have reacted with an aldehyde, preferably polyvinyl butyral, copolymers of acrylonitrile and acrylamide, polyacrylic acid esters, polymethacrylic acid esters, polystyrene and polyethylene or mixtures thereof. A particularly suitable polyvinyl butyral containing a minor amount of vinyl alcohol units is marketed under the trade name BUTVAR B79 of Monsanto USA and provides a good adhesion to paper and properly subbed polyester supports. It should be noted that there is no clear cut transition between a polymer dispersion and a polymer solution in the case of very small polymer particles resulting in the smallest particles of the polymer being dissolved and those slightly larger being in dispersion.

Suitable water-soluble polymers, according to the present invention, are: gelatin, gelatin derivatives, polyvinyl alcohol, polyacrylamide, polyacrylic acid, polymethacrylic acid, polyethyleneglycol, polysaccharides, such as starch, gum arabic and dextran and water-soluble cellulose derivatives.

To improve the layer-forming water-soluble and water-dispersible polymers, plasticizers can be incorporated into the polymers, water-miscible solvents can be added to the dispersion medium and mixtures of water-soluble polymers, mixtures of water-dispersible polymers, or mixtures of water-soluble and water-dispersible polymers may be used.

Thermal Solvents

The above mentioned binders or mixtures thereof may be used in conjunction with waxes or "heat solvents" also called "thermal solvents" or "thermosolvents" improving the reaction speed of the redox-reaction at elevated temperature.

By the term "heat solvent" in this invention is meant a non-hydrolyzable organic material which is in a solid state in the recording layer at temperatures below 50° C., but becomes a plasticizer for the recording layer where thermally heated and/or a liquid solvent for at least one of the redox-reactants, e.g. the reducing agent for the substantially light-insensitive organic heavy metal salt, at a temperature above 60° C. Useful for the purpose are the polyethylene glycols having a mean molecular weight in the range of 1,500 to 20,000 described in U.S. Pat. No. 3,347,675. Other suitable heat solvents are compounds such as urea, methyl sulfonamide and ethylene carbonate as described in U.S. Pat. No. 3,667,959; compounds such as tetrahydro-thiophene-1,1-dioxide, methyl anisate and 1,10-decanediol as described in Research Disclosure 15027 published in December 1976; and those described in U.S. Pat. Nos. 3,438,776, 4,740,446, 5,368,979, EP-A 0 119 615, EP-A 122 512 and DE-A 3 339 810.

Ratio of Binder to Organic Heavy Metal Salt

The weight ratio of binder to organic heavy metal salt is preferably in the range of 0.2 to 6, and the thickness of the recording layer is preferably in the range of 1 to 50 μm.

Toning Agents

In order to obtain a neutral black image tone in the higher densities and neutral grey in the lower densities, thermographic and photothermographic materials according to the present invention may contain one or more toning agents. The toning agents should be in thermal working relationship with the substantially light-insensitive heavy metal salts and reducing agents during thermal processing. Any known toning agent from thermography or photothermography may be used.

Suitable toning agents are phthalazine, succinimide and the phthalimides and phthalazinones within the scope of the general formulae described in U.S. Pat. No. 4,082,901 and the toning agents described in U.S. Pat. No. 3,074,809, U.S. Pat. No. 3,446,648 and U.S. Pat. No. 3,844,797. Particularly useful toning agents are the heterocyclic toner compounds of the benzoxazine dione or naphthoxazine dione type within the scope of following general formula are described in GB-P 1,439,478 and U.S. Pat. No. 3,951,660:

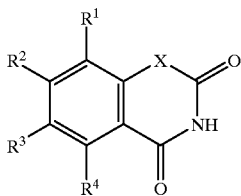

in which: X represents O or N-alkyl; each of $R^1$, $R^2$, $R^3$ and $R^4$ (same or different) represents hydrogen, alkyl, e.g. C1–C20 alkyl, preferably C1–C4 alkyl, cycloalkyl, e.g. cyclopentyl or cyclohexyl, alkoxy, preferably methoxy or ethoxy, alkylthio with preferably up to 2 carbon atoms, hydroxy, dialkylamino of which the alkyl groups have preferably up to 2 carbon atoms or halogen, preferably chlorine or bromine; or $R^1$ and $R^2$ or $R^2$ and $R^3$ represent the ring members required to complete a fused aromatic ring, preferably a benzene ring, or $R^3$ and $R^4$ represent the ring members required to complete a fused aromatic aromatic or cyclohexane ring.

A toner compound, according to the above general formula, particularly suited for use in combination with polyhydroxy benzene reducing agents is benzo[e][1,3]oxazine-2,4-dione.

Stabilizers and Antifoggants

In order to obtain improved shelf-life and reduced fogging, stabilizers and antifoggants may be present in the thermographic and photothermographic materials of the present invention. Examples of suitable stabilizers and antifoggants and their precursors, which can be used alone or in combination, include the thiazolium salts described in U.S. Pat. Nos. 2,131,038 and 2,694,716; the azaindenes described in U.S. Pat. Nos. 2,886,437 and 2,444,605; the urazoles described in U.S. Pat. No. 3,287,135; the sulfocatechols described in U.S. Pat. No. 3,235,652; the oximes described in GB-P 623,448; the thiuronium salts described in U.S. Pat. No. 3,220,839; the palladium, platinum and gold salts described in U.S. Pat. Nos. 2,566,263 and 2,597,915; the tetrazolyl-thio-compounds described in U.S. Pat. No. 3,700,457; the mesoionic 1,2,4-triazolium-3-thiolate stablizer precursors described in U.S. Pat. Nos. 4,404,390 and 4,351,896; the tribromomethyl ketone compounds described in EP-A 600 587; the combination of isocyanate and halogenated compounds described in EP-A 600 586; the vinyl sulfone and β-halo sulfone compounds described in EP-A 600 589; and those compounds mentioned in this context in Chapter 9 of "Imaging Processes and Materials, Neblette's 8th edition", by D. Kloosterboer, edited by J. Sturge, V. Walworth and A. Shepp, page 279, Van Nostrand (1989); in Research Disclosure 17029 published in June 1978; and in the references cited in all these documents.

Surfactants

Non-ionic, cationic or anionic surfactants may be used, according to the present invention, to produce aqueous dispersions I of particles comprising a substantially light-insensitive organic heavy metal salt A and aqueous dispersions II of particles comprising an organic heavy metal salt B and to disperse water-dispersible binders, such as polymer latexes, in aqueous media. A mixture of non-ionic and anionic surfactacts, of non-ionic and cationic surfactants, of cationic and anionic surfactants or of non-ionic, ionic, cationic and anionic surfactants may also be used, according to the present invention.

Support

The support for the thermographic and photothermographic recording materials according to the present invention may be transparent, translucent or opaque, e.g. having a white light reflecting aspect and is preferably a thin flexible carrier made e.g. from paper, polyethylene coated paper or transparent resin film, e.g. made of a cellulose ester, e.g. cellulose triacetate, corona and flame treated polypropylene, polystyrene, polymethacrylic acid ester, polycarbonate or polyester, e.g. polyethylene terephthalate or polyethylene naphthalate as disclosed in GB 1,293,676, GB 1,441,304 and GB 1,454,956. For example, a paper base substrate is present which may contain white reflecting pigments, optionally also applied in an interlayer between the recording material and the paper base substrate.

The support may be in sheet, ribbon or web form and subbed if needs be to improve the adherence to the thereon coated heat-sensitive recording layer.

Suitable subbing layers for improving the adherence of the thermosensitive element and the antistatic layer outermost backing layer of the present invention for polyethylene terephthalate supports are described e.g. in GB-P 1,234,755, U.S. Pat. Nos. 3,397,988; 3,649,336; 4,123,278 and 4,478,907 which relates to subbing layers applied from aqueous dispersion of sulfonated copolyesters, and further the subbing layers described in Research Disclosure published in Product Licensing Index, July 1967, p. 6.

Suitable pretreatments of hydrophobic resin supports are, for example, treatment with a corona discharge and/or attack by solvent(s), thereby providing a micro-roughening.

The support may be made of an opacified resin composition, e.g. polyethylene terephthalate opacified by means of pigments and/or micro-voids, and/or may be coated with an opaque pigment-binder layer, and may be called synthetic paper, or paperlike film. Information about such supports can be found in EP's 194 106 and 234 563 and U.S. Pat. Nos. 3,944,699, 4,187,113, 4,780,402 and 5,059,579. Should a transparent base be used, the base may be colourless or coloured, e.g. having a blue colour.

Antistatic Layer

In a preferred embodiment the recording material of the present invention an antistatic layer is applied to the outermost layer on the side of the support not coated with the thermosensitive element. Suitable antistatic layers therefor are described in EP-A's 444 326, 534 006 and 644 456, U.S. Pat. Nos. 5,364,752 and 5,472,832 and DOS 4125758.

Photosensitive Silver Halide

The photosensitive silver halide used in the present invention may be employed in a range of 0.1 to 35 mol percent of substantially light-insensitive organic heavy metal salt, with the range of 0.5 to 20 mol percent being preferred and the range of 1 to 12 mol percent being particularly preferred.

The silver halide may be any photosensitive silver halide such as silver bromide, silver iodide, silver chloride, silver bromoiodide, silver chlorobromoiodide, silver chlorobromide etc. The silver halide may be in any form which is photosensitive including, but not limited to, cubic, orthorhombic, tabular, tetrahedral, octagonal etc. and may have epitaxial growth of crystals thereon.

The silver halide used in the present invention may be employed without modification. However, it may be chemically sensitized with a chemical sensitizing agent such as a compound containing sulphur, selenium, tellurium etc., or a compound containing gold, platinum, palladium, iron, ruthenium, rhodium or iridium etc., a reducing agent such as a tin halide etc., or a combination thereof. The details of these procedures are described in T. H. James, "The Theory of the Photographic Process", Fourth Edition, Macmillan Publishing Co. Inc., New York (1977), Chapter 5, pages 149 to 169.

Emulsion of Particles Comprising an Organic Heavy Metal Salt and Photosensitive Silver Halide The silver halide may be added to the thermosensitive element in any fashion which places it in catalytic proximity to the substantially light-insensitive organic heavy metal salt. Silver halide and the substantially light-insensitive heavy metal salt of an organic compound which are separately formed, i.e. ex-situ or "preformed", in a binder can be mixed prior to use to prepare a coating solution, but it is also effective to blend both of them for a long period of time. Furthermore, it is effective to use a process which comprises adding a halogen-containing compound, such as organohalo-compounds, onium halides, onium polyhalides, alkali halides, alkaline earth halides and ammonium halides, to an organic silver salt to partially convert a substantially light-insensitive organic silver salt to silver halide as disclosed in U.S. Pat. No. 3,457,075. The organohalo-compounds, halide salts or polyhalide salts are used in quantities of between 0.1 and 35 mol % with respect to the quantity of substantially light-insensitive organic heavy metal salt, with quantities between 0.5 and 20 mol % being preferred and with quantities between 1 and 12 mol % being particularly preferred.

According to a preferred embodiment according to the present invention, particles of the photosensitive silver halide in the photo-addressable thermosensitive element are uniformly distributed over and between particles comprising a substantially light-insensitive organic heavy metal salt, at least 80% by number of the photosensitive silver halide particles having a diameter, determined by transmission electron microscopy, of $\leq 40$ nm.

Onium Halides and Polyhalides

According to the present invention photosensitive silver halide produced by reacting aqueous dispersions I of particles comprising a substantially light-insensitive organic silver salt with at least one onium salt with halide or polyhalide anions may be present.

Preferred oniums according to the present invention are organo-phosphonium, organo-sulphonium and organo-nitrogen onium cations, with heterocyclic nitrogen onium (e.g. pyridinium), quaternary phosphonium and ternary sulphonium cations being preferred. Preferred halide anions, according to the present invention, are chloride, bromide and iodide. Preferred polyhalide anions, according to the present invention, consist of chlorine, bromine and iodine atoms.

Onium cations, according to the present invention, may be polymeric or non-polymeric. Preferred non-polymeric onium salts for partial conversion of particles of substantially light-insensitive organic heavy metal salt into photosensitive silver halides according to the present invention are:

PC01=3-(triphenyl-phosphonium)propionic acid bromide perbromide
PC02=3-(triphenyl-phosphonium)propionic acid bromide
PC03=3-(triphenyl-phosphonium)propionic acid iodide

Spectral Sensitizer

The thermosensitive element of the photothermographic recording material, according to the present invention, may contain a spectral sensitizer, optionally together with a supersensitizer, for the silver halide. The silver halide may be spectrally sensitized with various known dyes including cyanine, merocyanine, styryl, hemicyanine, oxonol, hemioxonol and xanthene dyes optionally, particularly in the case of sensitization to infra-red radiation, in the presence of a so-called supersensitizer. Useful cyanine dyes include those having a basic nucleus, such as a thiazoline nucleus, an oxazoline nucleus, a pyrroline nucleus, a pyridine nucleus, an oxazole nucleus, a thiazole nucleus, a selenazole nucleus and an imidazole nucleus. Useful merocyanine dyes which are preferred include those having not only the above described basic nuclei but also acid nuclei, such as a thiohydantoin nucleus, a rhodanine nucleus, an oxazolidinedione nucleus, a thiazolidinedione nucleus, a barbituric acid nucleus, a thiazolinone nucleus, a malononitrile nucleus and a pyrazolone nucleus. In the above described cyanine and merocyanine dyes, those having imino groups or carboxyl groups are particularly effective. Suitable sensitizers of silver halide to infra-red radiation include those disclosed in the EP-A's 465 078, 559 101, 616 014 and 635 756, the JN's 03-080251, 03-163440, 05-019432, 05-072662 and 06-003763 and the U.S. Pat. Nos. 4,515,888, 4,639,414, 4,713,316, 5,258,282 and 5,441,866. Suitable supersensitizers for use with infra-red spectral sensitizers are disclosed in EP-A's 559 228 and 587 338 and in the U.S. Pat. Nos. 3,877,943 and 4,873,184.

According to a preferred embodiment of the present invention, the thermosensitive element of the photothermographic recording material further comprises a dye with maximum absorbance in the wavelength range 600 to 1100 nm.

Antihalation Dyes

In addition to the ingredients, the photothermographic recording material of the present invention may contain antihalation or acutance dyes which absorb light which has passed through the photosensitive layer, thereby preventing its reflection. Such dyes may be incorporated into the thermosensitive element or in any other layer comprising the photothermographic recording material of the present invention. The antihalation dye may also be bleached either thermally during the thermal development process, as disclosed in the U.S. Pat. Nos. 4,033,948, 4,088,497, 4,153, 463, 4,196,002, 4,201,590, 4,271,263, 4,283,487, 4,308,379, 4,316,984, 4,336,323, 4,373,020, 4,548,896, 4,594,312, 4,977,070, 5,258,274, 5,314,795 and 5,312,721, or photobleached after removable after the thermal development process, as disclosed in the U.S. Pat. Nos. 3,984,248, 3,988,154, 3,988,156, 4,111,699 and 4,359,524. Furthermore the anti-halation layer may be contained in a layer which can be removed subsequent to the exposure process, as disclosed in U.S. Pat. No. 4,477,562 and EP-A 491 457. Suitable antihalation dyes for use with infra-red light are described in the EP-A's 377 961 and 652 473, the EP-B's 101 646 and 102 781 and the U.S. Pat. Nos. 4,581,325 and 5,380,635.

Additional Ingredients

In addition to the ingredients the photothermographic recording material may contain other additives such as free organic carboxylic acids, antistatic agents, e.g. non-ionic antistatic agents including a fluorocarbon group as e.g. in $F_3C(CF_2)_6CONH(CH_2CH_2O)$—H, silicone oil, e.g. BAYSILONE Ol A (tradename of BAYER AG - GERMANY), ultraviolet light absorbing compounds, white light reflecting and/or ultraviolet radiation reflecting pigments, silica, and/or optical brightening agents.

Protective Layer

According to a preferred embodiment of the thermographic and photothermographic recording materials of the present invention, the thermosensitive element is coated with a protective layer to avoid local deformation of the thermosensitive element, to improve its resistance against abrasion and to prevent its direct contact with components of the apparatus used for thermal development.

The protective layer preferably comprises a binder, which may be solvent soluble (hydrophobic), solvent dispersible, water soluble (hydrophilic) or water dispersible. Among the hydrophobic binders polycarbonates as described in EP-A 614 769 are particularly preferred. Suitable hydrophilic binders are, for example, gelatin, polyvinylalcohol, cellulose derivatives and polysaccharides, lulose, hydroxypropylcellulose etc., with hardenable binders being preferred and polyvinylalcohol being particularly preferred.

A protective layer according to the present invention may be crosslinked. Crosslinking can be achieved by using crosslinking agents such as described in WO 95/12495 for protective layers, e.g. tetra-alkoxysilanes, polyisocyanates, zirconates, titanates, melamine resins etc., with tetraalkoxysilanes such as tetramethyl orthosilicate and tetraethylorthosilicate being preferred.

A protective layer according to the present invention may comprise in addition at least one solid lubricant having a melting point below 150° C. and at least one liquid lubricant in a binder, wherein at least one of the lubricants is a phosphoric acid derivative, further dissolved lubricating material and/or particulate material, e.g. talc particles, optionally protruding from the outermost layer. Examples of suitable lubricating materials are surface active agents, liquid lubricants, solid lubricants which do not melt during thermal development of the recording material, solid lubricants which melt (thermomeltable) during thermal development of the recording material or mixtures thereof. The lubricant may be applied with or without a polymeric binder.

Such protective layers may also comprise particulate material, e.g. talc particles, optionally protruding from the protective outermost layer as described in WO 94/11198. Other additives can also be incorporated in the protective layer e.g. colloidal particles such as colloidal silica.

Coating Techniques

The coating of any layer of the thermographic and photothermographic materials of the present invention may proceed by any coating technique e.g. such as described in Modern Coating and Drying Technology, edited by Edward D. Cohen and Edgar B. Gutoff, (1992) VCH Publishers Inc. 220 East 23rd Street, Suite 909 New York, N.Y. 10010, U.S.A.

Thermographic Recording Process

Thermographic imaging is carried by the image-wise application of heat either in analogue fashion by direct exposure through an image or by reflection from an image or in digital fashion pixel by pixel either by using an infra-red heat souce, for example with a Nd-YAG laser or other infra-red laser, or direct thermal imaging with a thermal head.

As described in "Handbook of Imaging Materials", edited by Arthur S. Diamond—Diamond Research Corporation—Ventura, Calif., printed by Marcel Dekker, Inc. 270 Madison Avenue, New York, N.Y. 10016 (1991), p. 498–502 in thermal printing image signals are converted into electric pulses and then through a driver circuit selectively transferred to a thermal printhead. The thermal printhead consists of microscopic heat resistor elements, which convert the electrical energy into heat via Joule effect. The electric pulses thus converted into thermal signals manifest themselves as heat transferred to the surface of the thermal paper wherein the chemical reaction resulting in colour development takes place. The operating temperature of common thermal printheads is in the range of 300 to 400° C. and the heating time per picture element (pixel) may be 50 ms or less, the pressure contact of the thermal printhead with the recording material being e.g. 100–500 g/cm$^2$ to ensure a good transfer of heat.

In order to avoid direct contact of the thermal printing heads with a recording material not provided with an outermost protective layer, the imagewise heating of the recording material with the thermal printing heads may proceed through a contacting but removable resin sheet or web wherefrom during the heating no transfer of recording material can take place.

In a particular embodiment of the method according to the present invention the direct thermal image-wise heating of the recording material proceeds by Joule effect heating in that selectively energized electrical resistors of a thermal head array are used in contact or close proximity with the recording layer. Suitable thermal printing heads are e.g. a Fujitsu Thermal Head (FTP-040 MCS001), a TDK Thermal Head F415 HH7-1089 and a Rohm Thermal Head KE 2008-F3.

Activation of the heating elements can be power-modulated or pulse-length modulated at constant power.

EP-A 622 217 discloses a method for making an image using a direct thermal imaging element in which improvements in continuous tone reproduction are obtained by activating the heating elements line by line with a duty cycle Δ, representing the ratio of activation time to total line time, in such a way that the following equation is satisfied :

$$P \leq P_{max} = 3.3 \text{ W/mm}^2 + (9.5 \text{ W/mm}^2 \times \Delta)$$

wherein $P_{max}$ is the maximal value over all the heating elements of the time averaged power density P (expressed in W/mm$^2$) dissipated by a heating element during a line time.

Photothermographic Recording Process

Photothermographic materials, according to the present invention, may be exposed with radiation of wavelength between an X-ray wavelength and a 5 microns wavelength with the image either being obtained by pixel-wise exposure with a finely focussed light source, such as a CRT light source; a UV, visible or IR wavelength laser, such as a He/Ne-laser or an IR-laser diode, e.g. emitting at 780 nm, 830 nm or 850 nm; or a light emitting diode, for example one emitting at 659 nm; or by direct exposure to the object itself or an image therefrom with appropriate illumination e.g. with UV, visible or IR light.

For the thermal development of image-wise exposed photothermographic recording materials, according to the present invention, any sort of heat source can be used that enables the recording materials to be uniformly heated to the development temperature in a time acceptable for the application concerned e.g. contact heating, radiative heating, microwave heating etc.

Applications

The thermographic and photothermographic recording materials of the present invention can be used for both the production of transparencies and reflection type prints. This means that the support will be transparent or opaque, e.g. having a white light reflecting aspect. For example, a paper base substrate is present which may contain white reflecting pigments, optionally also applied in an interlayer between the recording material and the paper base substrate. Should a transparent base be used, the base may be colourless or coloured, e.g. has a blue colour.

In the hard copy field thermographic and photothermographic recording materials on a white opaque base are used, whereas in the medical diagnostic field black-imaged transparencies are widely used in inspection techniques operating with a light box.

The following examples and comparative examples illustrate the present invention. The percentages and ratios used in the examples are by weight unless otherwise indicated.

INVENTION EXAMPLE 1

Preparation of an Aqueous Dispersion of Silver Salicylate

An aqueous solution of sodium salicylate was prepared by adding 43.2 g of 2N sodium hydroxide to 12 g of salicylic acid in 240 g of demineralized water. This aqueous solution was simultaneously added with 120 mL of a 0.588 M aqueous solution of silver nitrate over a period of 10 s to 280 mL of a stirred aqueous solution containing 160 mL of a 5% aqueous solution of GAFAC ™ RM710 (an alkylphenyl-polyethene oxide-phosphate from GENERAL ANILINE), 80 mL of a 2% aqueous solution of NATRASOL™ 250L (a hydroxyethylcellulose from AQUALON) and 40 mL of demineralized water. 160 mL of a 5% aqueous solution of PIGMENTVERTEILER™ N (a sodium salt of polyacrylic acid from BASF) was then added to the resulting dispersion.

Preparation of an Aqueous Dispersion of Silver Benzotriazolate 45 mL of a 20% aqueous solution of benzotriazole with a pH of about 6.5 were added with stirring to the aqueous dispersion of silver salicylate. A fine dispersion of silver benzotriazolate was obtained. The size of the silver benzotriazolate particles was ascertained by optical microscopy to be 1 to 2 $\mu$m.

Desalination of the Aqueous Dispersion of Silver Benzotriazolate

The sodium nitrate formed in this process was removed by precipitating the silver benzotriazolate by acidifying with sulphuric acid to a pH of 2.5, decanting off the aqueous solution, washing the precipitate with demineralized water and then peptizing the precipitate in demineralized water by increasing the pH to 6.5 with a dilute solution of sodium hydroxide. A salt-free fine dispersion of 1 to 2 $\mu$m silver benzotriazolate particles in 300 mL of water was obtained, as determined by examination under a microscope.

INVENTION EXAMPLE 2

24 mL of a 0.294 M aqueous solution of potassium bromide was mixed with 8 mL of a 0.294 M aqueous solution of potassium iodide. This mixture was then added to a silver benzotriazolate dispersion prepared as described in INVENTION EXAMPLE 1, whereupon part of the silver benzotriazolate was converted into silver halide.

The dispersion was then desalinated in an analagous fashion to that described in INVENTION EXAMPLE 1, a dispersion of 1 to 2 $\mu$m particles of partially converted silver benzotriazolate being obtained.

INVENTION EXAMPLE 3

288 mL of a 8.9% solution of sodium behenate in an aqueous isoprapanol solution containing 16.7% by volume of isopropanol at a temperature of 78° C. were added to the silver salicylate dispersion, prepared as described in INVENTION EXAMPLE 1, forming a fine dispersion of silver behenate.

INVENTION EXAMPLE 4

A silver behenate in a dispersion prepared as described in INVENTION EXAMPLE 3 was partially converted to silver halide in an analogous way to that described for silver benzotriazolate in INVENTION EXAMPLE 2. A fine dispersion of partially converted silver behenate was obtained.

INVENTION EXAMPLE 5

A silver salicylate dispersion was prepared as described in INVENTION EXAMPLE 1 except that after silver salicylate formation 160 mL of a 5% aqueous solution of ACYLIDONE™ ACP1041 (a copolymer of acrylic acid and polyvinylpyrrolidone from ISP) was added instead of 160 mL of a 5% aqueous solution of PIGMENTVERTEILER ™ N.

The silver benzotriazolate dispersion preparation and the desalination thereof were then carried out as described in INVENTION EXAMPLE 1.

INVENTION EXAMPLE 6

Coating a Support with a Thermosensitive Layer 0.3 mL of a 30% solution of phthalazine and 2 mL of a 30% solution of ascorbic acid were added to 30 mL of a desalinated silver benzotriazolate dispersion prepared as in INVENTION EXAMPLE 1. The resulting dispersion was then doctor blade coated onto a subbed 100 $\mu$m polyethene terephthalate support to a wet layer thickness of 70 $\mu$m and dried to produce a thermographic material.

Thermographic Printing

The printer was equipped with a thin film thermal head with a resolution of 300 dpi and was operated with a line time of 19 ms (the line time being the time needed for printing one line). During the line time the print head received constant power. The average printing power, being the total amount of electrical input energy during one line time divided by the line time and by the surface area of the heat-generating resistors was 1.5 mJ/dot being sufficient to obtain maximum optical density in each of the recording materials.

During printing the print head was separated from the imaging layer by a thin intermediate material contacted with a slipping layer of a separable 5 $\mu$m thick polyethylene terephthalate ribbon coated successively with a subbing layer, heat-resistant layer and the slipping layer (anti-friction layer) giving the ribbon with a total thickness of 6 $\mu$m.

Image Evaluation

The optical maximum density of the print obtained with the recording material of INVENTION EXAMPLE 6 by measurement through a visual filter with a Macbeth™

TR924 densitometer of the grey scale step corresponding to the data level of 255 was 1.2.

INVENTION EXAMPLE 7

Coating a Support with a Photo-addressable Thermosensitive Layer 0.3 mL of a 30% solution of phthalazine and 2 mL of a 30% solution of ascorbic acid were added to 30 mL of a desalinated partially converted silver benzotriazolate dispersion prepared as in INVENTION EXAMPLE 2. The resulting dispersion was then doctor blade coated onto a subbed 100 μm polyethene terephthalate support to a wet layer thickness of 70 μm and dried to produce a photothermographic material.

Image-wise Exposure and Thermal Processing

The photothermographic material was then exposed to ultra-violet light through a test original in contact with the material in an Agfa-Gevaert™ DL 2000 exposure apparatus. Thermal development was carried out in pressure contact with a metal block at 104° C. for 15 s. The image obtained had a good image quality.

COMPARATIVE EXAMPLE 1

Preparation of a Silver Benzotriazolate Directly from Benzotriazole 160 ml of a 5% aqueous solution of GAFAC™ RM710 (an alkylphenyl-polyethene oxide-phosphate from GENERAL ANILINE) and 80 mL of a 2% aqueous solution of NATRASOL™ 250 L (a hydroxyethylcellulose from AQUALON) were added to 120 mL of a 0.588 M aqueous solution of silver nitrate (a salt with a solubility in water of 69.5 g per 100 mL at 20° C.) and then 323 mL of demineralized water and 160 mL of a 5% aqueous solution of PIGMENTVERTEILER™ N (a sodium salt of polyacrylic acid from BASF) were added.

45 mL of a 20% solution of benzotriazole in ethanol were then added were stirring to the above described solution. A flocculated precipitate of silver benzotriazolate was obtained, illustrating the benefit of the two stage preparation procedure according to the present invention.

Having described in detail preferred embodiments of the current invention, it will now be apparent to those skilled in the art that numerous modifications can be made therein without departing from the scope of the invention as defined in the following claims.

What is claimed is:

1. A process for producing an aqueous dispersion containing particles of a substantially light insensitive silver salt A, said silver salt A being a salt of a carboxylic acid having a solubility of less than $10^{-3}$ g in 100 ml of water at 20° C., said process consisting essentially of:
   (a) preparing an aqueous dispersion containing particles of a silver salt B, said silver salt B having a solubility of between 0.001 g and 1.5 g in 100 ml of water at 20° C., wherein the media for said aqueous dispersion is selected from the group consisting of water and mixtures of water and water-miscible organic solvents; and
   (b) reacting said particles of said silver salt B in the aqueous dispersion formed in step (a) with a solution of a conversion agent, wherein said conversion agent is a water soluble salt of the carboxylic acid, thereby forming the aqueous dispersion of particles of said substantially light insensitive silver salt A.

2. The process according to claim 1 wherein said light insensitive silver salt A is silver behenate.

3. A process for producing an aqueous dispersion containing particles of a substantially light insensitive silver salt A, wherein said silver salt A is a salt of an organic compound with an acidic N—H group having a solubility of less than $10^{-3}$ g in 100 ml of water at 20° C., said process consisting essentially of:
   (a) preparing an aqueous dispersion containing particles of a silver salt B, said silver salt B having a solubility of between 0.001 g and 1.5 g in 100 ml of water at 20° C., wherein the media for said aqueous dispersion is selected from the group consisting of water and mixtures of water and water-miscible organic solvents;
   (b) reacting said particles of said silver salt B in the aqueous dispersion formed in step (a) with a solution of a conversion agent wherein said conversion agent is a water soluble salt of the organic compound with an acidic N—H group, thereby forming the aqueous dispersion of particles of said substantially light insensitive silver salt A.

4. The process according to claim 3, wherein said light insensitive silver salt A is silver benzotriazolate.

5. The process according to claim 3, wherein said silver salt B is silver salicylate.

6. A process for producing a thermographic material comprising a thermosensitive element coated from an aqueous dispersion containing particles of a substantially light insensitive silver salt A, said silver salt A being a salt of an organic compound with an acidic N—H group, said process consisting essentially of:
   (i) preparing an aqueous dispersion containing particles of a silver salt B, said silver salt B having a solubility of between 0.001 g and 1.5 g in 100 ml of water at 20° C.,
   (ii) reacting said particles of said silver salt B in the dispersion produced in step (i) with a solution of a conversion agent, said conversion agent being a water soluble salt of the organic compound with an acidic N—H group, thereby forming the aqueous dispersion of particles of said substantially light insensitive silver salt A, wherein a particle size from 1 to 2 μm is obtained and said silver salt A has a solubility of less than $10^{-3}$ g in 100 ml of water at 20° C.;
   (iii) coating onto a support one or more aqueous dispersions or solutions which together include said aqueous dispersion of the light insensitive silver salt A particles resulting from step (ii), an organic reducing agent and a binder including a water-dispersible binder, a water-soluble binder or any mixture thereof, wherein the media for said aqueous dispersions or solutions are selected from the group consisting of water and mixtures of water and water-miscible organic solvents; and
   (iv) drying the resulting one or more coatings to produce the thermosensitive element.

7. The process according to claim 6, wherein said thermosensitive element further comprises photosensitive silver halide in catalytic association with said light insensitive salt A.

8. The process according to claim 6, wherein said thermosensitive element is coated with a protective layer.

9. The process according to claim 6 wherein said light insensitive silver salt A is silver benzotriazolate.

10. A process for producing a thermographic material comprising a thermosensitive element coated from an aqueous dispersion containing particles of a substantially light insensitive silver salt A, said silver salt A being a salt of a carboxylic acid, said process consisting essentially of:

(i) preparing an aqueous dispersion containing particles of a silver salt B, said silver salt B having a solubility of between 0.001 g and 1.5 g in 100 ml of water at 20° C.;

(ii) reacting said particles of said silver salt B in the dispersion produced in step (i) with a solution of a conversion agent, said conversion agent being a water soluble salt of the carboxylic acid, thereby forming the aqueous dispersion of particles including the substantially light insensitive silver salt A, wherein the silver salt A has a solubility of less than $10^{-3}$ g in 100 ml of water at 20° C.;

(iii) coating onto a support one or more aqueous dispersions or solutions which together include the aqueous dispersion of the light insensitive silver salt A particles resulting from step (ii), an organic reducing agent and a binder including a water-dispersible binder, a water-soluble binder or any mixture thereof, wherein the media for said aqueous dispersions or solutions are selected from the group consisting of water and mixtures of water and water-miscible organic solvents;

(iv) drying the resulting one or more coatings to produce the thermosensitive element.

11. The process according to claim 10, wherein said thermosensitive element further comprises photosensitive silver halide in catalytic association with said light insensitive silver salt A.

12. The process according to claim 10, wherein said thermosensitive element is coated with a protective layer.

* * * * *